US010488334B2

(12) United States Patent
Iyechika

(10) Patent No.: US 10,488,334 B2
(45) Date of Patent: Nov. 26, 2019

(54) GROWTH-RATE MEASURING APPARATUS AND GROWTH-RATE DETECTION METHOD

(71) Applicant: NuFlare Technology, Inc., Kanagawa (JP)

(72) Inventor: Yasushi Iyechika, Chiba (JP)

(73) Assignee: NuFlare Technology, Inc., Kanagawa (JP)

(*) Notice: Subject to any disclaimer, the term of this patent is extended or adjusted under 35 U.S.C. 154(b) by 0 days.

(21) Appl. No.: 15/946,045

(22) Filed: Apr. 5, 2018

(65) Prior Publication Data

US 2018/0292315 A1    Oct. 11, 2018

(30) Foreign Application Priority Data

Apr. 6, 2017   (JP) ................................ 2017-076216

(51) Int. Cl.
   *G01N 21/41*    (2006.01)
   *G01N 21/84*    (2006.01)
   (Continued)

(52) U.S. Cl.
   CPC ....... *G01N 21/4133* (2013.01); *C23C 14/547* (2013.01); *C23C 16/52* (2013.01);
   (Continued)

(58) Field of Classification Search
   CPC .... G01N 21/4133; G01N 21/31; G01N 21/45; G01N 21/55; G01N 21/8422;
   (Continued)

(56) References Cited

U.S. PATENT DOCUMENTS

| 5,756,375 | A | * | 5/1998 | Celii | B24B 37/013 |
| | | | | | 257/E21.109 |
| 6,048,742 | A | * | 4/2000 | Weyburne | H01L 21/67253 |
| | | | | | 438/16 |

(Continued)

FOREIGN PATENT DOCUMENTS

| JP | 8193813 A2 | 7/1996 |
| JP | 933223 | 2/1997 |

(Continued)

OTHER PUBLICATIONS

W. G. Breiland et al., "A Virtual Interface Method for Extracting Growth Rates and High Temperature Optical Constants from Thin Semiconductor Films Using In Situ Normal Incidence Reflectance", J. Appl. Phys. 78 (1995), pp. 1-26.

(Continued)

*Primary Examiner* — Isiaka O Akanbi
(74) *Attorney, Agent, or Firm* — Rankin, Hill & Clark LLP

(57) ABSTRACT

A growth-rate measuring apparatus has a refractometer to irradiate light of a plurality of different wavelengths to a surface of a substrate to measure a reflectivity of the surface of the substrate per different wavelengths, a fitter to fit a reflectivity calculated by a model function, the model function being obtained in advance, to a measured value of the reflectivity, for at least one layer of thin films laminated one by one on the substrate, with at least one of a refractive index and a growth rate as a fitting parameter, a parameter extractor to extract sets of fitting parameters for each wavelength in the different wavelengths, respectively, for which an error between the calculated reflectivity and the measured value of the reflectivity is minimum, and a parameter selector to select an optimum set of values of the fitting parameter, (Continued)

among the fitting parameters extracted for the different wavelengths.

17 Claims, 13 Drawing Sheets

(51) Int. Cl.
  *H01L 21/66* (2006.01)
  *C23C 16/52* (2006.01)
  *H01L 21/67* (2006.01)
  *G01N 21/31* (2006.01)
  *G01N 21/45* (2006.01)
  *G01N 21/55* (2014.01)
  *C23C 14/54* (2006.01)

(52) U.S. Cl.
  CPC ............ *G01N 21/31* (2013.01); *G01N 21/45* (2013.01); *G01N 21/55* (2013.01); *G01N 21/8422* (2013.01); *H01L 21/67253* (2013.01); *G01N 2021/4126* (2013.01); *G01N 2021/551* (2013.01); *G01N 2021/8438* (2013.01); *H01L 22/12* (2013.01)

(58) Field of Classification Search
  CPC ..... G01N 2021/4126; G01N 2021/551; G01N 2021/8438; C23C 14/547; C23C 16/52; H01L 21/67253; H01L 22/12
  USPC .......................................... 356/445, 364, 497
  See application file for complete search history.

(56) References Cited

U.S. PATENT DOCUMENTS

| | | | |
|---|---|---|---|
| 6,275,297 B1* | 8/2001 | Zalicki ................... | G01N 21/31 356/496 |
| 2007/0188768 A1* | 8/2007 | Mansfield .......... | G01B 11/0675 356/504 |
| 2015/0211934 A1* | 7/2015 | Van Mechelen .......... | G01J 5/10 250/339.06 |
| 2016/0130696 A1* | 5/2016 | Price ....................... | C23C 14/54 427/10 |

FOREIGN PATENT DOCUMENTS

| | | |
|---|---|---|
| JP | 9181131 A2 | 7/1997 |
| JP | 10190153 A2 | 7/1998 |
| JP | 2010258207 A2 | 11/2010 |
| JP | 5050044 A | 10/2012 |
| JP | 2017143241 A2 | 8/2017 |

OTHER PUBLICATIONS

O. Reentilä et al., "In situ determination of nitrogen content in InGaAsN quantum wells", Journal of Applied Physics 100, 013509, 2006, total 5 pages.

Hyunseok Na et al., "In-Situ, Real-Time Spectral Reflectance Monitoring of GaN Growth", Journal of the Korean Physical Society, vol. 37, No. 6, Dec. 2000, pp. 971-974.

* cited by examiner

GROWTH-RATE MEASURING APPARATUS AND GROWTH-RATE DETECTION METHOD

CROSS REFERENCE TO RELATED APPLICATIONS

This application is based upon and claims the benefit of priority from the prior Japanese Patent Application No. 2017-76216, filed on Apr. 6, 2017, the entire contents of which are incorporated herein by reference.

FIELD

Embodiments relate to a growth-rate measuring apparatus and a growth-rate detection method.

BACKGROUND

As methods for forming a uniform thin film over a wide area with excellent reproducibility, vapor phase deposition methods, such as metal organic chemical vapor deposition (MOCVD), molecular beam epitaxy (MBE), and sputtering, are well known. These methods are important as an industrial thin-film forming method. As a method for observing, in situ, an optical constant, a growth rate, etc. of a thin film formed by these vapor deposition methods, a method for monitoring change in light reflectivity with time is known. In this method, light beam is radiated to a measurement target formed with a thin film through an optical window provided on a wall surface of a thin-film forming apparatus to measure a reflectivity of light beam in a predetermined wavelength during a film formation process. When the surface of a substrate, on which a thin film is to be formed, is a mirror surface, for light radiated to the thin film, due to an interference effect between reflected light on the surface of the formed thin film and reflected light on the interface between the substrate and the thin film, an observed reflectivity periodically varies with respect to the thin-film thickness. The optical constant, film thickness, etc. of a formed thin film can be calculated from the cycle of reflectivity change to the film thickness, the minimum and maximum values of the reflectivity, and so on. Moreover, the growth rate can be calculated from a thin-film forming time.

A popular procedure of the above-described calculation will be explained hereinbelow. A thin-film reflectivity can be measured by a reflectometer. On the contrary, reflectivity change with time can be simulated with calculation of an appropriate function (hereinafter, referred to as a reflectivity model function, as required) using parameters, such as a growth rate, a refractive index, etc. of a formed thin film. By determining (fitting) a result of simulation using the above-listed parameters so as to have a minimum error in comparing the result of simulation with measured values of reflectivity change with time by the reflectometer, a fitting parameter in the reflectivity model function can be selected. However, a plurality of error minimum points may appear in the case of fitting the reflectivity model function to reflectivity measured values, and hence it is not easy to determine which minimum point is the correct solution.

DETAILED DESCRIPTION

According to one embodiment, a growth-rate measuring apparatus has:

a refractometer to irradiate light of a plurality of different wavelengths to a surface of a substrate to measure reflectivity of the surface of the substrate per different wavelengths;

a fitter to fit the reflectivity calculated by a model function, the model function being obtained in advance, to a measured value of the reflectivity, for at least one layer of thin films laminated one by one on the substrate, with at least one of a refractive index and a growth rate as a fitting parameter;

a parameter extractor to extract sets of fitting parameters for each wavelength in the different wavelengths, respectively, for which an error between the reflectivity calculated by the model function and the measured value of the reflectivity is minimum; and a parameter selector to select an optimum set of values of the fitting parameters, among the fitting parameters extracted for the different wavelengths.

Hereinafter, embodiments of the present disclosure will be explained with reference to the drawings. In the accompanying drawings of the present specification, for simplicity of drawings and easy understanding, the scale, the ratio of height to width, etc. are appropriately modified or enlarged from actual ones.

Terms used in this specification to define shapes and geometrical conditions, and also their degrees, for example, such as "parallel", "orthogonal" and "the same", the values of length and angle, etc. are, not to be limited to the strict sense of the terms, but interpreted to such an extent that a similar function can be expected.

Figure 1:
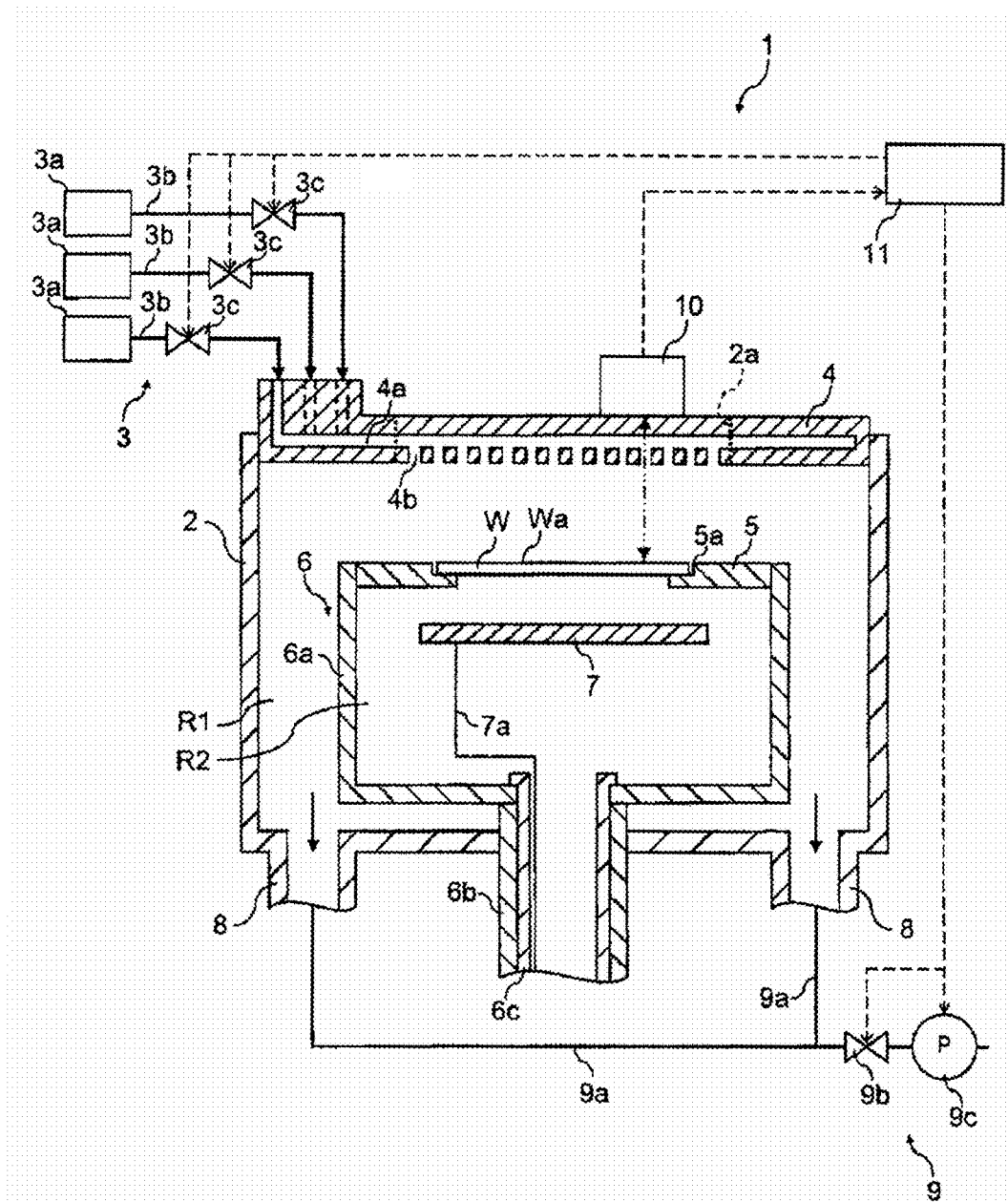
FIG. 1 is a drawing schematically showing a configuration of a vapor phase deposition apparatus according to a first embodiment.

FIG. 1 is a drawing schematically showing a configuration of a vapor deposition apparatus 1 according to a first embodiment. In the present embodiment, an example will be explained in which, as a substrate to be subjected to film formation, a silicon substrate, specifically, a silicon wafer (merely referred to as a wafer, hereinafter) W is used, and a single film or a plurality of thin films are laminated on the wafer W in film formation. Hereinafter, an explanation will be made with MOCVD as an example of a vapor phase deposition method. Although the present embodiment is applicable to substrates other than the silicon substrate, the substrate surface is required to be a mirror surface. Moreover, as the method of laminating a plurality of thin films on the substrate surface, not only MOCVD, but other methods can be used.

The vapor deposition apparatus 1 of FIG. 1 is provided with a chamber 2 for film formation on the wafer W, a gas supplier 3 for supplying a source gas to the wafer W in the chamber 2, a source discharger 4 located above the chamber 2, a susceptor 5 for holding the wafer W in the chamber 2, a rotating part 6 that rotates while holding the susceptor 5, a heater 7 for heating the wafer W, a gas exhauster 8 for exhausting a gas in the chamber 2, an exhaust mechanism 9 for exhausting a gas from the gas exhauster 8, a radiation thermometer 10 for measuring a temperature of the wafer W, and a controller 11 for controlling the component parts.

The chamber 2 has a shape (such as a cylindrical shape) capable of accommodating the wafer W to be subjected to film formation. The chamber 2 accommodates the susceptor 5, the heater 7, part of the rotating part 6, etc.

The gas supplier 3 has a plurality of gas storages 3a for respectively storing a plurality of gases, a plurality of gas pipes 3b for connecting the gas storages 3a and the source discharger 4, and a plurality of gas valves 3c for adjusting flow rates of gases that flow through the gas pipes 3b. Each gas valve 3c is connected to the associated gas pipe 3b. The gas valves 3c are controlled by the controller 11. There are a plurality of configurations for actual piping, such as, coupling a plurality of gas pipes, making one gas pipe to branch to a plurality of gas pipes, and a combination of gas-pipe branching and coupling.

Source gases supplied from the gas supplier 3 pass through the source discharger 4 and are discharged into the chamber 2. The source gases (process gases) discharged into the chamber 2 are supplied onto the wafer W, and, accordingly, a desired film is formed on the wafer W. There is no particular limitation on the types of source gases to be used.

A shower plate 4a is provided on the bottom side of the source discharger 4. The shower plate 4a can be configured with a metal material such as stainless steel and an aluminum alloy. Gases from the gas pipes 3b are mixed one another in the source discharger 4 and pass through gas jetting ports 4b of the shower plate 4a, and then are supplied into the chamber 2. A plurality of gas passages may be provided to the shower plate 4a so as to supply a plurality of types of gases, as being separated from one another, to the wafer W in the chamber 2.

The structure of the source discharger 4 should be selected in view of uniformity of a formed film, material efficiency, reproducibility, production cost, etc. However, there is no particular limitation on the structure, as long as the selected one meets those requirements. Known structures can also be used as required.

The susceptor 5 is provided on the rotating part 6 to hold the wafer W in such a manner that the wafer W is placed in a counterbore provided in the inner peripheral side of the susceptor 5. In the example of FIG. 1, the susceptor 5 is formed into an annular shape with an opening at its center, however, may be formed into a roughly flat shape without the opening.

The heater 7 is a heating part for heating the susceptor 5 and/or the wafer W, with no particular limitation as long as meeting the requirements of the capability of heating a heating target at a desired temperature and in desired temperature distribution, durability, etc. As examples, specifically, resistance heating, lamp heating, induction heating, etc. are listed up.

The exhaust mechanism 9 exhausts a reacted source gas from the inside of the chamber 2 via the gas exhauster 8 and controls the pressure inside the chamber 2 to a desired pressure with the operations of an exhaust valve 9b and a vacuum pump 9c.

The radiation thermometer 10 is provided on the upper surface of the source discharger 4. The radiation thermometer 10 irradiates light from a light source to the wafer W and receives reflected light from the wafer W to measure a reflected light intensity of the wafer W. As described, the radiation thermometer 10 functions as a reflectometer to measure a reflectivity of a film growing surface. Moreover, the radiation thermometer 10 receives thermal radiation light from a film growing surface Wa of the wafer W to measure a thermal radiation light intensity. The radiation thermometer 10 has a built-in data arithmetic unit that acquires the temperature of the wafer W from the thermal radiation light intensity and reflectivity. The data arithmetic unit can be configured, for example, with a general purpose computer.

A light transmission window 2a is provided on the upper surface of the source discharger 4. Light from a light source of the radiation thermometer 10, and reflected light and thermal radiation light each from the wafer W pass through the light transmission window 2a. The light transmission window 2a may be formed into any shape such as a slit shape, a rectangular shape, and a circular shape. A member used for the window is transparent in a wavelength range of light to be measured by the radiation thermometer 10. In the case of measuring the temperature from a room temperature to about 1500° C., it is preferable to measure a wavelength of light in the range from a visible range to a near infrared range. In this case, as a window member, quartz glass is preferably used.

The controller 11 is provided with a computer for centralized control of component parts of the film forming apparatus 1 and a storage unit for storing film formation information related to film formation, a several types of programs, etc. Based on the film formation information, the several types of programs, etc., the controller 11 controls the gas supplier 3, the rotation mechanism of the rotating part 6, the exhaust mechanism 9, etc. to control the heating of the wafer W by the heater 7, and the like. In addition, the controller 11 has a function of a growth-rate measuring apparatus 21 according to the present embodiment. The growth-rate measuring apparatus 21 may be provided in the vapor deposition apparatus 1 of FIG. 1, apart from the controller 11. In this case, the growth-rate measuring apparatus 21 is connected to the controller 11. The internal configuration and operation of the growth-rate measuring apparatus 21 will be described later.

Figure 2:
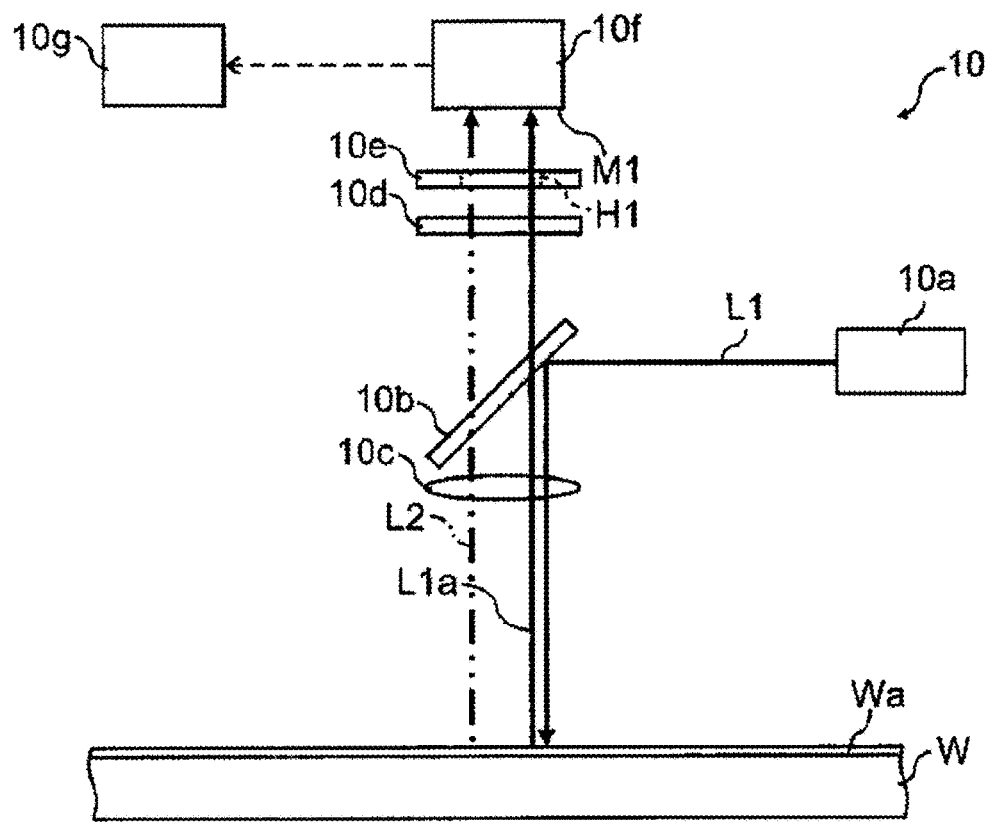
FIG. 2 is a drawing showing an internal configuration of a radiation thermometer.

FIG. 2 is a drawing showing an internal configuration of the radiation thermometer 10. The radiation thermometer 10 has a light source 10a, a half mirror 10b, a focus adjustment lens 10c, a wavelength selective filter 10d, a diaphragm 10e, a photoreceptor 10f, and a thermometer controller 10g.

The light source 10a emits illumination light L1 to be radiated to the wafer W. The half mirror 10b reflects and directs the illumination light L1 to the wafer W, and passes light from the wafer W therethrough. The focus adjustment lens 10c makes the illumination light L1, which has passed through the half mirror 10b, focused on the wafer W. Furthermore, the focus adjustment lens 10c makes reflected light L1a and thermal radiation light L2 from the wafer W focused on a photoreception surface M1 of the photoreceptor 10f. The wavelength selective filter 10d passes therethrough reflected light L1a and thermal radiation light L2 that have passed through the half mirror 10b, in a predetermined wavelength range. The diaphragm 10e passes therethrough light only from a portion of the wafer W, the portion being required for measurements. The photoreceptor 10f receives the reflected light L1a and thermal radiation light L2 that have passed through the diaphragm 10e. The thermometer controller 10g acquires the temperature of the wafer W based on the intensity of the reflected light L1a (reflected light intensity) and the intensity of the thermal radiation light L2 (thermal radiation intensity), received by the photoreceptor 10f.

The radiation thermometer 10 irradiates light in a relatively wide wavelength range to a measurement target and observes reflected light in a predetermined wavelength range using a wavelength selective filter. This is because the thermal radiation intensity is also required to be measured in the predetermined wavelength. On the contrary, when acquiring the reflectivity only, a method of irradiating light of a predetermined wavelength to a measurement target to measure its reflected light intensity, can be used. The above-described light of a predetermined wavelength can be acquired by passing light of a relatively wide wavelength range through a wavelength selective filter which passes only light of a predetermined wavelength therethrough. Or light from a light source of high mono chromaticity, such as a laser beam, may be used.

The reflectivity measured by the radiation thermometer 10 can be used as measured data of reflectivity in the present embodiment. Moreover, a dedicated reflectivity measuring apparatus to be used in the present embodiment may be provided to a vapor phase deposition apparatus. In addition, in an apparatus for measuring substrate warpage, it is general to irradiate light of high directivity such as a laser beam to a substrate. Such a warpage measuring apparatus can measure a reflected light intensity while observing the warpage. Reflectivity data measured by such a warpage measuring apparatus can also be used as measured reflectivity data in the present embodiment.

The vapor deposition apparatus 1 according to the present embodiment can be used for formation of a variety of films on the wafer W. However, hereinafter, as an example, growth rate measurements in the case where an AlN layer and an SLS (Strained Layer Superlattice) structure, in which AlGaN thin films and AlN thin films are alternately laminated, are formed on a silicon wafer W, will be explained.

(Basic Principle of Present Embodiment)

Hereinafter, a basic principle of the present embodiment will be explained. In a process of forming one or a plurality of thin films on a substrate surface that is a mirror surface, when light of a given wavelength is irradiated onto a thin film surface, reflected light from the thin film surface and reflected light from the substrate surface interfere with each other, so that the reflectivity of interference light changes with time. The reflectivity change cycle depends on the wavelength of light irradiated onto the thin film. In more specifically, interference light cycle is expressed by $2nd/\lambda$ where n is a refractive index of a thin film, d is a film thickness of the thin film, and $\lambda$ is a wavelength of light to be irradiated.

Figure 3:
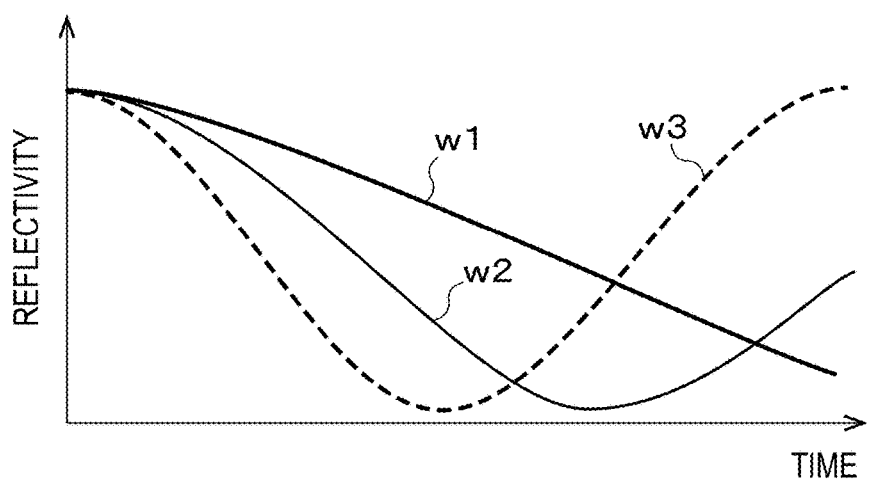
FIG. 3 is a waveform diagram showing change in reflectivity of interference light with time.

FIG. 3 is a waveform diagram showing change in reflectivity of interference light with time. In FIG. 3, the abscissa is time and the ordinate is reflectivity. FIG. 3 shows three reflectivity waveforms w1 to w3 that correspond to light of three wavelengths irradiated onto a thin film surface, showing an example in which w2 is shorter than w1 in wavelength and w3 is shorter than w2 in wavelength. As understood from FIG. 3, as the wavelength is longer, the reflectivity shows a moderate change with time.

Figure 4:
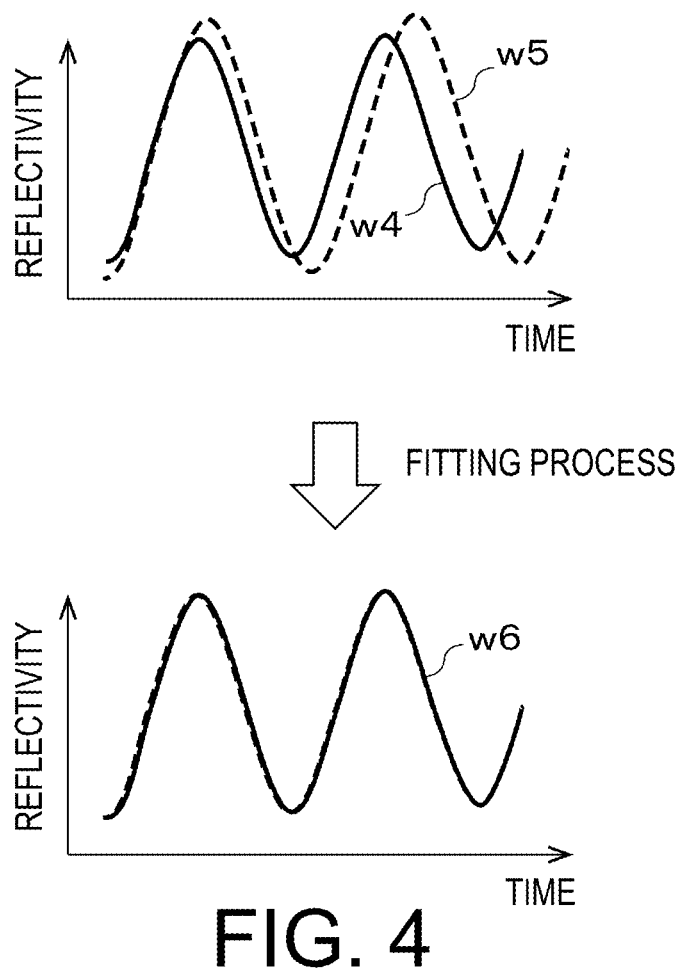
FIG. 4 is a drawing showing the outline of a process performed by a growth-rate measuring apparatus according to the present embodiment.

FIG. 4 is a drawing showing the outline of a process performed by the growth-rate measuring apparatus 21 according to the present embodiment. In FIG. 4, a waveform w4 is a reflectivity change with time measured by a refectrometer and a waveform w5 is a reflectivity change with time acquired by simulation (reflectivity model function). In FIG. 4, the abscissa is time and the ordinate is reflectivity. In the present embodiment, a process of matching the waveform w5 with the waveform w4 (hereinafter, referred to as fitting) is performed by adjusting a set of values of fitting parameters (simply referred to as fitting parameter(s) or the like, hereinafter) of the reflectivity model function. A waveform w6 is an example of fitting the waveform w5 to the waveform w4.

Figure 5:
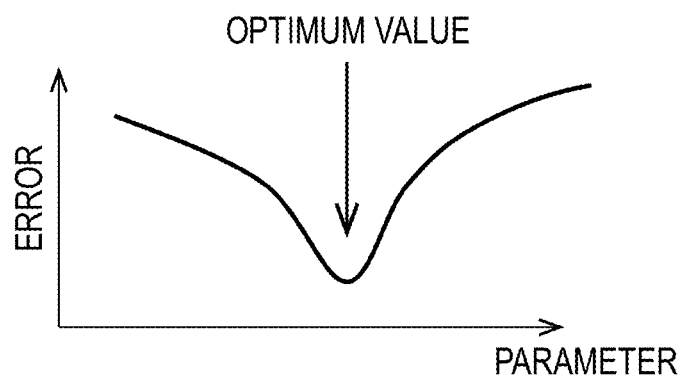
FIG. 5 is a drawing explaining an error minimum value.

As a result of above, as shown in FIG. 5, an error between the reflectivity model function and the reflectivity measured by the refectrometer becomes minimum at the best fitting, the minimum point being referred to as an optimum value. Although FIG. 5 shows just one parameter used in fitting for simplicity, actually many parameters are used, and the above-mentioned error is a multidimensional function of these parameters.

Figure 6A:
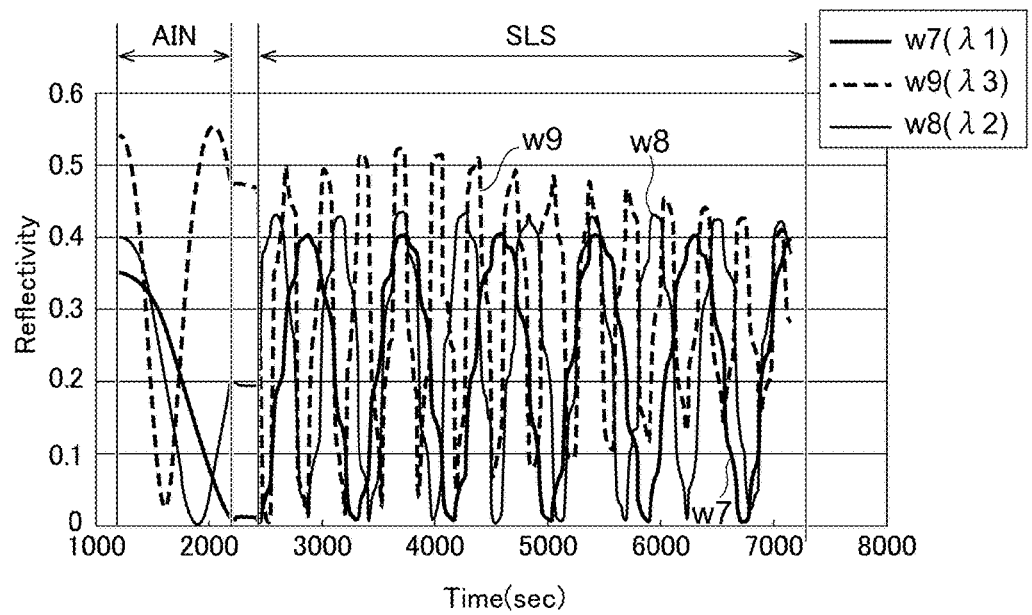
FIG. 6A is a graph showing reflectivity change with time in the case of laminating an AlN layer and an SLS.

FIG. 6A is a graph that shows measured reflectivity change with time for an AlN layer functioning as a buffer layer and for an SLS that is a laminated film of AlN thin films and AlGaN thin films alternately laminated after the growth of the AlN layer. In FIG. 6A, graphs w7 to w9 show reflectivity change with time measured by the refrectometer. The graphs w7 to w9 show results of radiation of light in wavelengths $\lambda 1$ to $\lambda 3$, respectively.

Figure 6B:
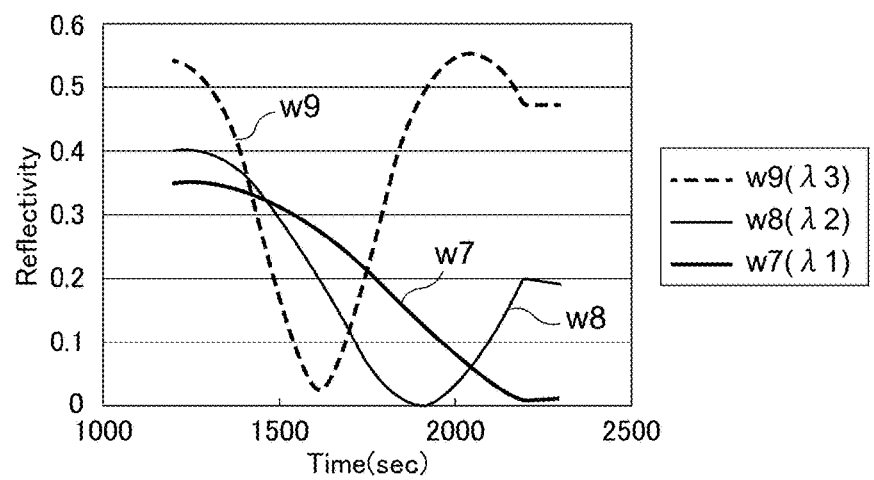
FIG. 6B is an enlarged graph of reflectivity change with time for the portion where the AlN layer is formed.
Figure 6C:
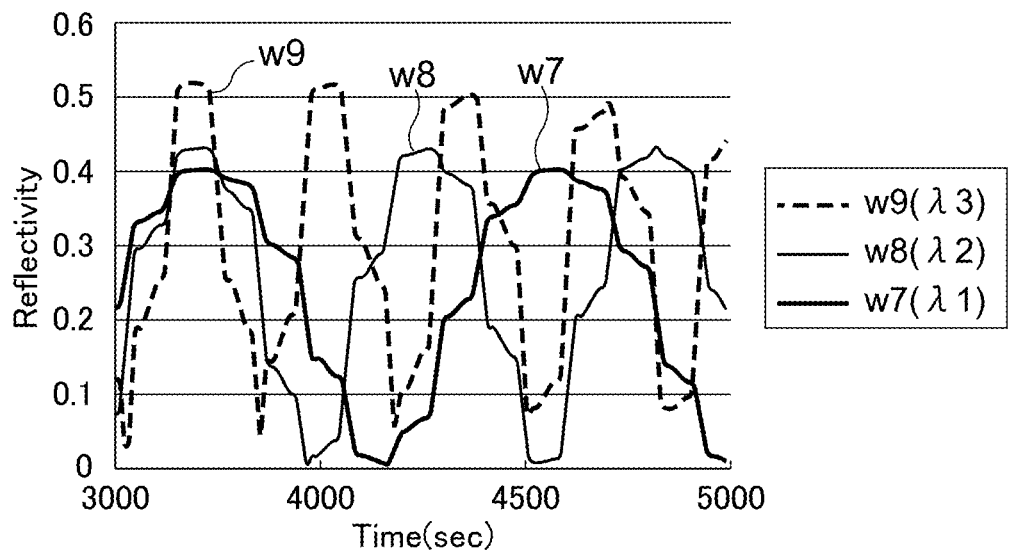
FIG. 6C is an enlarged graph of reflectivity change with time for the portion where the SLS is formed.

FIG. 6B shows enlarged graphs of reflectivity change with time at the time of lamination of the AlN layer functioning as the buffer layer. FIG. 6C shows enlarged graphs of reflectivity change with time at the time of SLS lamination.

Figure 7:
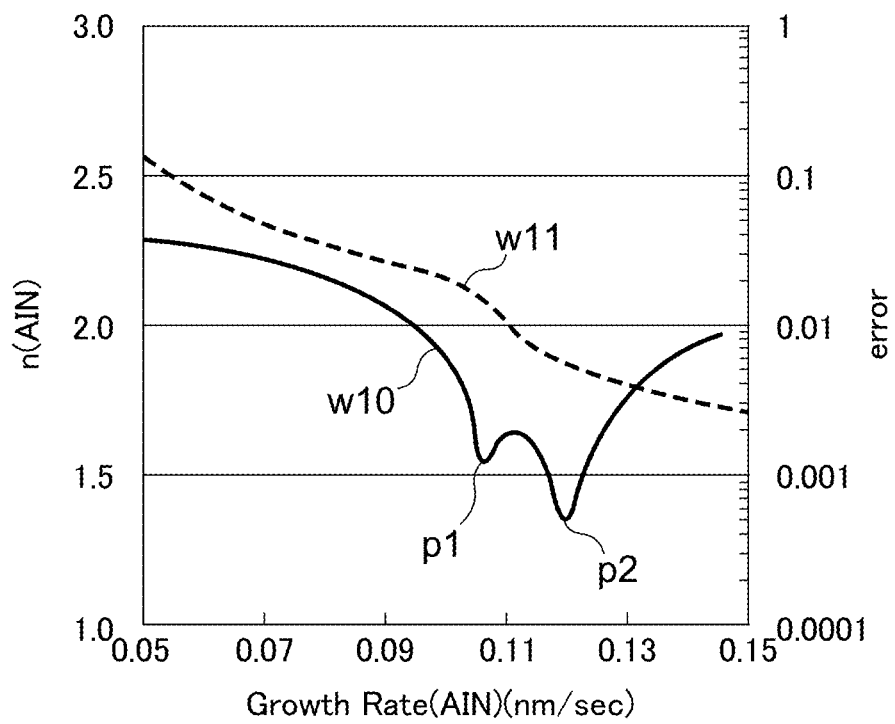
FIG. 7 is a drawing showing a relationship of an error and of a refractive index to a growth rate in the case of using light of a wavelength $\lambda 1$.

FIG. 7 shows a relationship of an error, in the case of fitting the reflectivity model function to the measured values of reflectivity of the AlN layer at the wavelength $\lambda 1$ shown in FIG. 6B, and also a relationship of a reflective index acquired by the fitting, to the growth rate (curves w10 and w11, respectively).

The abscissa and ordinate for the error curve w10 are a growth rate (nm/sec) of the AlN layer and an error amount, respectively. The abscissa and ordinate for the reflective index curve w11 are the growth rate (nm/sec) of the AlN layer and a reflective index n, respectively.

A calculation method of the error and reflective index shown in FIG. 7 will be explained hereinafter. In the case of growing the AlN layer shown in FIG. 6B, the reflectivity change with time is expressed by four parameters that are real part and imaginary part of a complex refractive index of a substrate on which the AlN layer is grown, and refractive index and growth rate of AlN. Although, usually, fitting is performed simultaneously to the four parameters, in order to make clear the relationships between a fitting error and the growth rate, and between a refractive index acquired by fitting and the growth rate, the growth rate among the four fitting parameters is fixed to a certain value and fitting is performed to the other three parameters. In this way, it is determined to what level, the error decreases at a certain growth rate and then the acquired value of refractive index in the case. FIG. 7 shows the error and the refractive index plotted with respect to the growth rate, which were acquired by the above-described procedure performed to a large number of growth rate values. In FIG. 7, minimum values p1 and p2 on the error curve w10 are expected to give the same result with the minimum values in the case of fitting the four parameters simultaneously.

The above-described complex refractive index of the substrate is virtual. In detail, it is known that the reflectivity change, in the case where a thin film is further formed on a single-layer film or a multi-layer film, is equivalent to the reflectivity change in the case where a layer under a formed thin film is a single layer having a virtual complex refractive index. As described, a reflectivity calculation method, in the case where a layer, on which a thin film is formed, is treated as a single layer having a virtual complex refractive index, is referred to as a virtual interface method or the like.

In the errors on the error curve w10, there are two minimum points p1 and p2. The minimum points p1 and p2 indicate growth rates in the case where fitting between a reflectivity calculated with a reflectivity model function and a reflectivity measured by the reflectometer is most appropriate. Although in the minimum points p1 and p2, either one is considered to correspond to an actual growth rate, in view of errors included in reflectivity measurements, it cannot be determined in principle only from a result of FIG. 7 which of p1 and p2 is a correct solution.

There are different AlN refractive indexes at the two minimum points p1 and p2. At the minimum point p2 where the growth rate is much higher, the refractive index is below 2.0 that is lower than an actual AlN-layer refractive index. It is therefore found that the minimum point p2 is not a correct solution for estimating an AlN-layer growth rate, and it can be estimated that the growth rate at the minimum point p1 is a correct solution.

Figure 8:
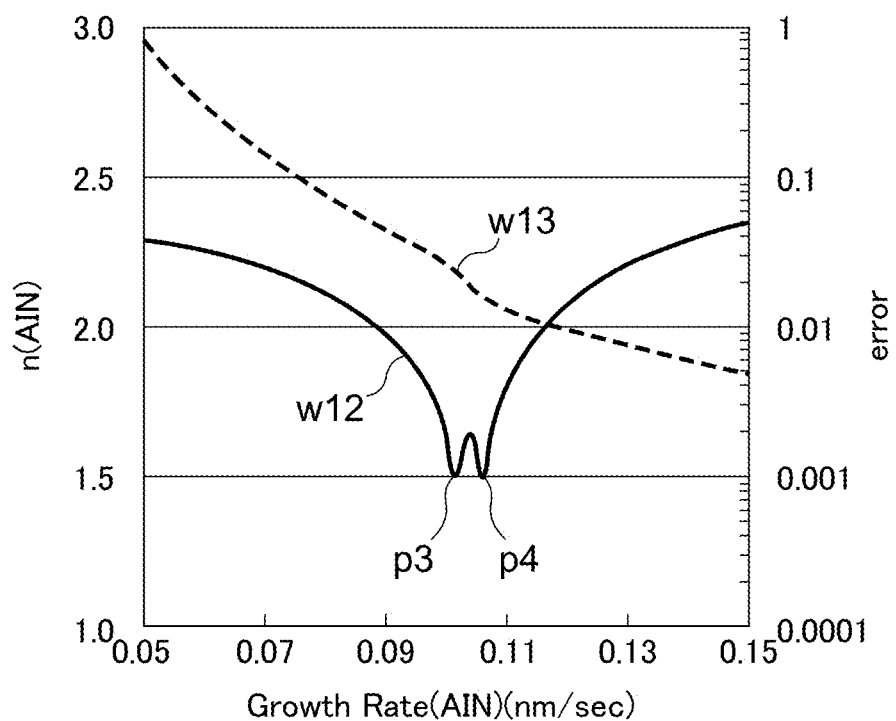
FIG. 8 is a drawing showing a relationship of an error and of a refractive index to a growth rate in the case of using light of a wavelength $\lambda 2$.

FIG. 8 shows an error curve w12 of an error in the case of fitting performed with light of the wavelength $\lambda 2$ different from that in FIG. 7 and a refractive index curve w13 obtained by fitting. Also in FIG. 8, there are two minimum points p3 and p4 in the error curve w12. However, the refractive indexes at the minimum points p3 and p4 both exceed 2.0, so that it cannot be determined only from FIG. 8 which of the minimum points p3 and p4 is a correct solution.

Figure 9:
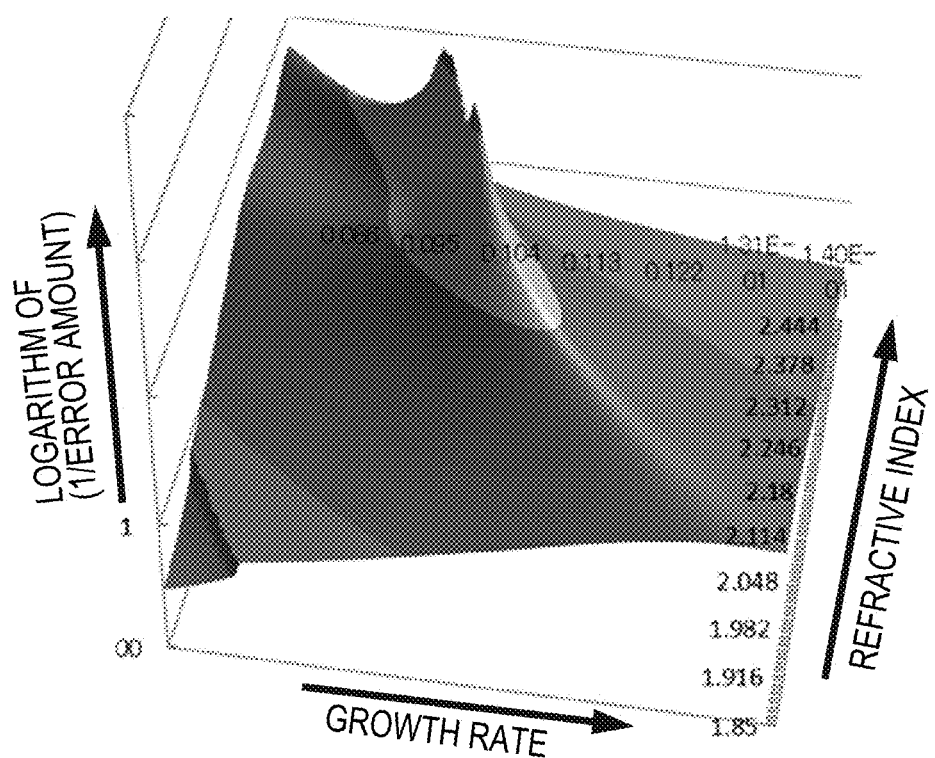
FIG. 9 is a drawing showing a relationship of the error to the growth rate and to the refractive index using light of the wavelength $\lambda 2$, expressed by a three-dimensional image.

FIG. 9 is a drawing of an error amount in the case of fitting performed with light of the wavelength $\lambda 2$, expressed by a three-dimensional image. In this case, fitting was performed with the growth rate and refractive index being fixed to certain values, among the four parameters to be used in fitting. FIG. 9 indicates the relationship of the errors obtained by fitting for combinations of many growth rates and refractive indexes, to the growth rate and also to the refractive index. In FIG. 9, the x-, y- and z-axes are the growth rate, refractive index, and logarithm of (1/error amount), respectively. It is indicated that, as the value on the z-axis is larger, the error amount is smaller. Except that the z-axis is scaled in a different way, in principle, the projection of an edge portion in FIG. 9 in the growth-rate axis direction gives those shown in FIG. 8. The peak positions in the three-dimensional image of FIG. 9 are the minimum points of FIG. 8. Fitting of actual four parameters can be said to search for a parameter set, with which the error becomes minimum, from a given starting point (a set of initial values of parameters). It is understood that a final error peak point from the starting point in FIG. 9 changes depending on initial values of parameters to be used in fitting.

Figure 10:
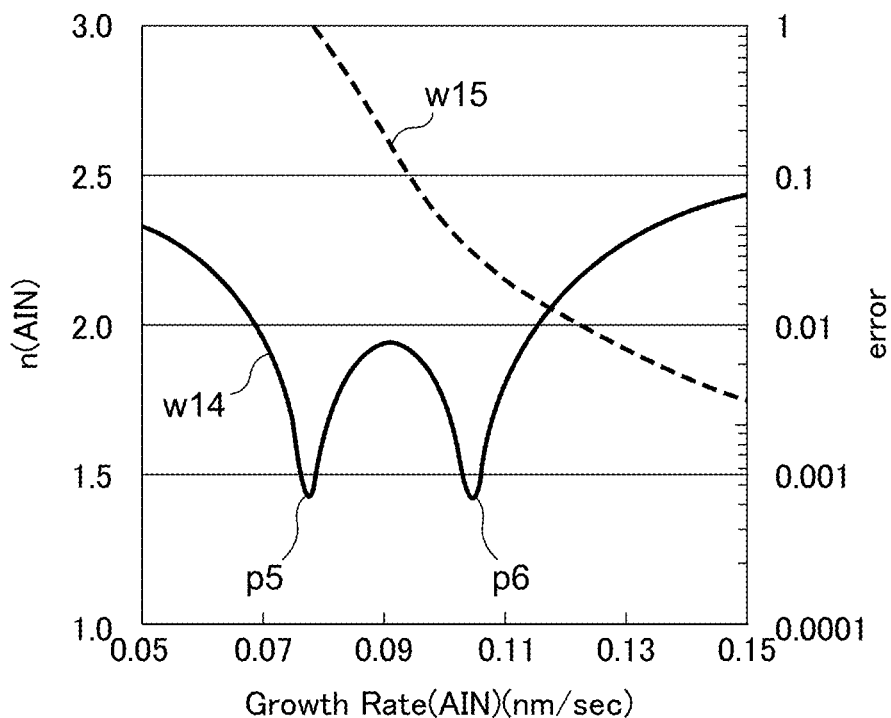
FIG. 10 is a drawing showing a relationship of an error and of a refractive index to a growth rate in the case of using light of a wavelength $\lambda 3$.

FIG. 10 shows an error curve w14 in the case of fitting performed with light of the wavelength $\lambda 3$ different from those in FIGS. 7 and 8, and a refractive index curve w15 obtained by fitting. Also in FIG. 10, there are two minimum points p5 and p6. However, the refractive index at the minimum point p5 largely exceeds 2.5 that is the upper limit of AlN refractive index in view of measurement errors, and hence is not a correct solution. Therefore, it can be predicted that a growth rate at the minimum point p6 is a correct solution.

As described, there is a case where, when the reflectivity model function is fitted to a reflectivity measured by the reflectometer, there are a plurality of positions (sets of values of fitting parameters) where the error is minimum. In this case, there is a possibility that it cannot be easily determined which set of the plurality of fitting parameters is a correct solution. In such a case, if refractive index information is already known, there is a possibility that a correct parameter can be selected by removing incorrect solutions. It might be also possible to select a correct set of fitting parameters by comparison with a result of measurement using X-ray diffraction, other measuring instrument such as an ellipsometer, etc. However, there are problems such that an adaptive range of analyzing method used in combination with as described above is limited, several types of measurement must to be performed, which takes time, etc.

In view of above, in the present embodiment, a process of using each light of a plurality of wavelengths to fit the reflectivity model function to a reflectivity measured by the reflectometer is performed to extract an error minimum point per wavelength and compare the positions of the minimum points in the plurality of wavelengths, to select a set of fitting parameters. In this way, without using information such as the refractive index or without using other measuring instrument, a fitting parameter can be selected by, for example, software processing.

Figure 11:
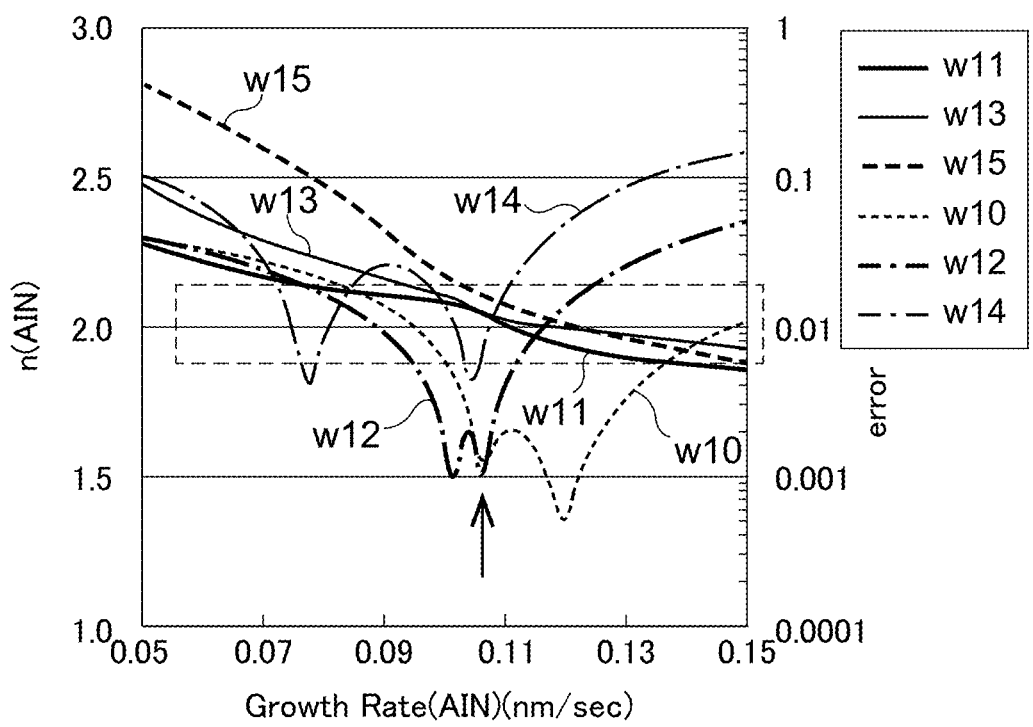
FIG. 11 is a drawing showing a relationship of an error and of a refractive index to a growth rate in the case of using light of the wavelengths $\lambda 1$, $\lambda 2$ and $\lambda 3$.

FIG. 11 is a drawing of the error curves at the three wavelengths $\lambda 1$, $\lambda 2$ and $\lambda 3$, and the corresponding refractive index curves superimposed on one another. In FIG. 11, the abscissa is a growth rate (nm/sec) and the ordinate is an error amount or a refractive index value. Although, the growth rate at which an error is minimum is different per wavelength, a minimum point indicated by an arrow in FIG. 11 is shared by the three error curves. It is therefore found out that the growth rate on the position of this minimum point is a correct solution. In the above-described steps of acquiring a correct solution, any knowledge about the refractive index of a material (AlN) to be formed into a film is not required.

As described above, error minimum points are extracted using a plurality of wavelengths and, when a position on each of the error curves where the error minimum points match one another for the wavelengths, is found out, a fitting parameter on the position can be selected as a correct solution.

In other words, the above-described steps can be said that change with time in the reflectivity of a substrate on which a thin film is being laminated is measured for a plurality of different wavelengths, a minimum point is extracted per wavelength by reflectivity model-function fitting, and the extracted minimum points are compared among the wavelengths to select a correct solution.

Figure 12:
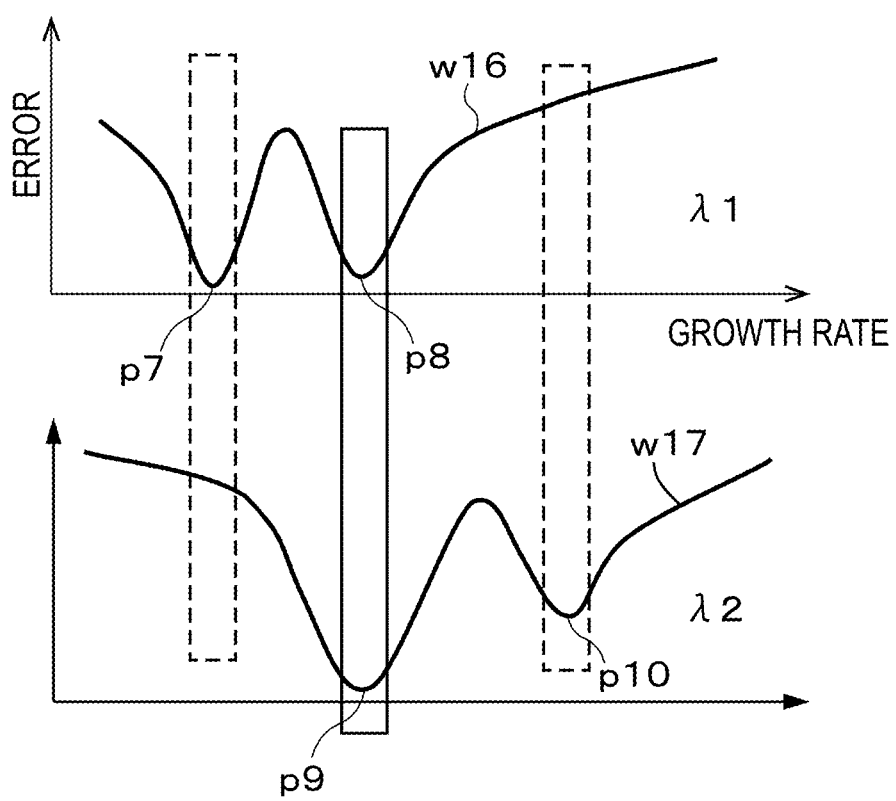
FIG. 12 is a drawing showing error curves in the case of using light of the wavelengths $\lambda 1$ and $\lambda 2$.

Although, in FIG. 11, the selection of fitting parameters is performed using three wavelengths, the selection of fitting parameters can be performed based on a result of extraction of minimum points at at least two wavelengths. FIG. 12 is a drawing for explaining the selection of a thin-film growth rate that is a fitting parameter, using two wavelengths. FIG. 12 schematically shows error curves w16 and w17 using two wavelengths $\lambda 1$ and $\lambda 2$, respectively. The error curve w16 corresponding to light of the wavelength $\lambda 1$ has two minimum points p7 and p8, and the error curve w17 corresponding to light of the wavelength $\lambda 2$ has also two minimum points p9 and p10. Among the minimum points, the minimum points p8 and p9 match each other on the growth rate that is the fitting parameter. The fitting parameter can be selected by means of the parameter values at the minimum points p8 and p9.

As described above, according to the present embodiment, even in the case where a plurality of minimum points appear on an error curve at one wavelength, so that it cannot be determined which of the minimum points is a correct solution, by using a plurality of wavelengths, a minimum point, which is a correct solution, can be selected.

In the above-described method, in order to extract every minimum point at one wavelength, fitting is performed to each point of a narrowly-divided growth rate. In this method, the number of times of fitting to be performed is the number of the divided points of the growth rate, and hence it is difficult to perform a minimum-point extraction operation in a short time. Accordingly, fitting may be performed using the fitting parameters that include the growth rate in a range of growth rate divided into necessary sections in advance. For example, when it is considered that there are three minimum points in a given range of growth rate, the above given range of growth rate is divided into appropriate numbers of sections of three or more, and within the divided growth rate range, fitting is performed using the fitting parameters including the growth rate. In this way, while drastically reducing the number of times of fitting in the above-described steps, it is possible to extract necessary minimum points. Although, in the above explanation, the growth rate is mentioned as an example of a parameter whose range is to be divided, another parameter may be used as the parameter whose range is to be divided.

Figure 13:
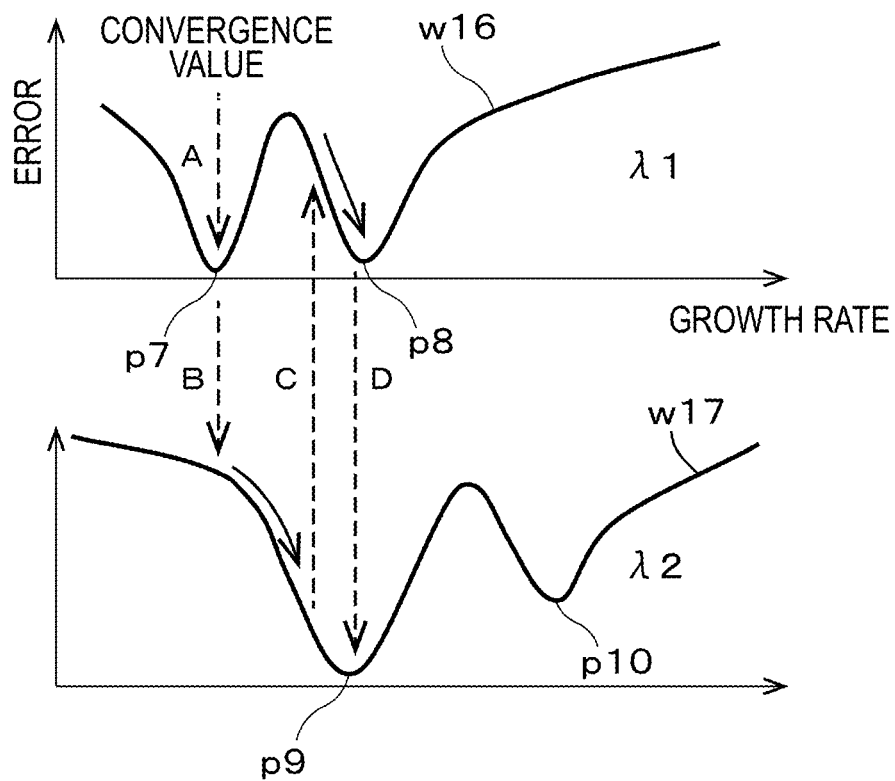
FIG. 13 is a drawing that explains a process of finding out a minimum point, which is a correct solution, among minimum points on an error curve.

FIG. 13 is a drawing that explains another process of selecting a minimum point, which is a correct solution, among minimum points on an error curve, using light of the two wavelengths $\lambda 1$ and $\lambda 2$. The relationship between the error and the growth rate (w16 and w17) of FIG. 13 is shown to help understanding the following fitting steps, with no need to know the relationship in advance. When the error and the growth rate have the relationship shown in FIG. 13, actual fitting starts from a certain parameter initial value. By examining the relationship between a parameter (here, the growth rate) near the initial value and the error, an approximate optimum value of the parameter can be estimated. Based on the estimated value of the parameter optimum value obtained in this way, estimation of the optimum value is performed again. By repeating this operation, a parameter value with which the error becomes minimum can be finally found out even if the relationship between an actual error and the parameter is not known entirely.

Returning to the explanation of FIG. 13, a first minimum point is extracted by fitting on an error curve w16 with light of the wavelength $\lambda 1$ (A in FIG. 13). In this way, when a minimum point p7 is extracted, subsequently, with a parameter value (for example, a growth rate at the minimum point p7) at the minimum point p7 as a starting point, the next minimum point is extracted by fitting on an error curve w17 with light of the wavelength $\lambda 2$ (B in FIG. 13). At a predetermined point near a minimum point p9, fitting is performed with a parameter value at this point to extract the next minimum point on the error curve with light of the wavelength $\lambda 1$ (C in FIG. 13). In this way, when a minimum point p8 is extracted, it is examined whether a parameter value at the minimum point p8 is a minimum point on the error curve with light of the wavelength $\lambda 2$ (D in FIG. 13). If it is the minimum point, it is decided that the position where the minimum points on both error curves match each other is found out, and the parameter value at this minimum point is selected as a correct parameter. An advantage of this method is when a minimum point extracted at one wavelength is not a minimum point at another wavelength (in the case of an incorrect parameter), by performing fitting at the next wavelength, fitting is automatically moved from an initial parameter (parameter extracted as a minimum point at the first wavelength) to another minimum point. This method is not required to extract every minimum point in advance, so that the steps can be drastically simplified.

In other words, the above-described steps are performed as follows. Change with time in reflectivity of a substrate, on which a thin film is being laminated, is measured with a plurality of different wavelengths to extract one minimum point at one wavelength and it is examined whether the extracted minimum point is a minimum point at another wavelength. As a result of examination, if it is judged that the extracted minimum point is the minimum point at the other wavelength, this solution is selected as a correct solution. On the other hand, if the minimum point extracted first is not the minimum point at the other wavelength, a minimum point at the other wavelength is newly extracted. For the newly extracted minimum point, the above-described operation is performed at a further another wavelength different from the other wavelength. The operation is repeated until a correct solution is selected.

In the above-described steps, fitting may be divided for the case where not so high accuracy is required for removing an incorrect minimum point and for the case where the parameter is finally determined precisely. In order to simplify the steps, for fitting with no high accuracy required, restricting the number of times of repeated calculation in fitting, lowering the determination criterion for determining that a minimum point is reached, etc. may be performed.

Specifically, an example of the method, which examines whether parameter values (growth rate in FIG. 13) which give error minimum points (p8 and p9 in FIG. 13) are the same at different wavelengths, examines whether difference between parameter values extracted at different wavelengths are in a predetermined range. In order to finally determine a parameter at high accuracy, fitting may be performed simultaneously at a plurality of wavelengths.

(Outline of Growth-Rate Measuring Apparatus 21)

As described above, the growth-rate measuring apparatus 21 according to the present embodiment may be built in the controller 11 of FIG. 1. In this case, the controller 11 may be provided with the growth-rate measuring apparatus 21 as a hardware configuration or may achieve the function of the growth-rate measuring apparatus 21 with software processing.

Figure 14:
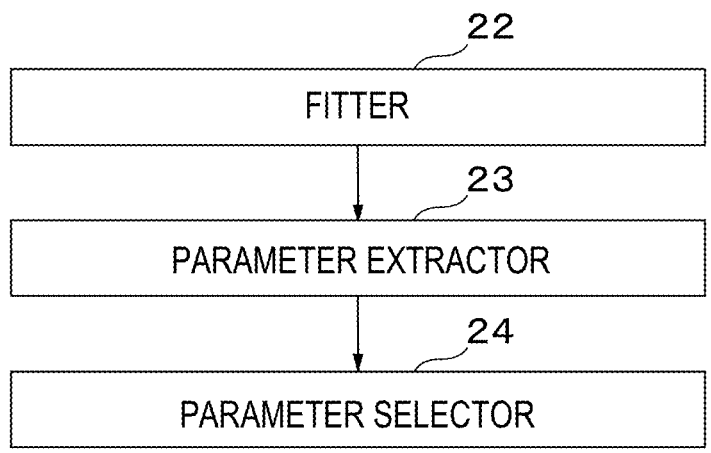
FIG. 14 is a block diagram showing an internal configuration of a growth-rate measuring apparatus.

FIG. 14 is a block diagram showing an internal configuration of the growth-rate measuring apparatus 21. As shown in FIG. 14, the growth-rate measuring apparatus 21 has a fitter 22, a parameter extractor 23, and a parameter selector 24. A reflectivity measured by the reflectometer is input to the growth-rate measuring apparatus 21.

The fitter 22 fits a reflectivity calculated by the model function to measured reflectivity values, with a fitting parameter that is at least one of a refractive index and a growth rate of at least one layer of thin films laminated on a substrate one by one. In other words, the fitter 22 performs parameter fitting to find out an optimum value. In more detail, based on a result of measuring reflectivities with light of a plurality of wavelengths, the fitter 22 adjusts a set of fitting parameters that includes at least one of a refractive index and a growth rate of at least one layer of thin films laminated on a substrate one by one, and fits a reflectivity model function to a measured reflectivity values for each of the plurality of wavelengths or simultaneously for the plurality of wavelengths.

The parameter extractor 23 extracts a set of fitting parameters with which an error between the reflectivity model function and the measured reflectivity values becomes minimum, for each of the plurality of wavelengths. In other words, the parameter extractor 23 lists up one or a plurality of optimum values.

The parameter selector 24 compares the fitting parameters extracted for the plurality of wavelengths with one another to select a fitting parameter. For example, the parameter selector 24 examines the plurality of wavelengths one by one to select a set of fitting parameters from sets of fitting parameters extracted for each wavelength with which an error is minimum for the different wavelengths (selection).

In other words, the parameter selector 24 selects a most appropriate one among the optimum values listed up for each wavelength.

As another specific example, the parameter extractor 23 may perform to extract a first set of fitting parameters with which an error is minimum for a first wavelength among a plurality of wavelengths and then extract a second set of fitting parameters with which an error is minimum for a second wavelength different from the first wavelength, based on the first set of fitting parameters. Moreover, in the case where the first set of fitting parameters and the second set of fitting parameters match each other, the parameter selector 24 may decide the set of fitting parameters, as an optimum one. Furthermore, the parameter extractor 23 may repeat fitting for the first wavelength and fitting for the second wavelength until a set of fitting parameters is selected by the parameter selector 24.

Figure 15A:
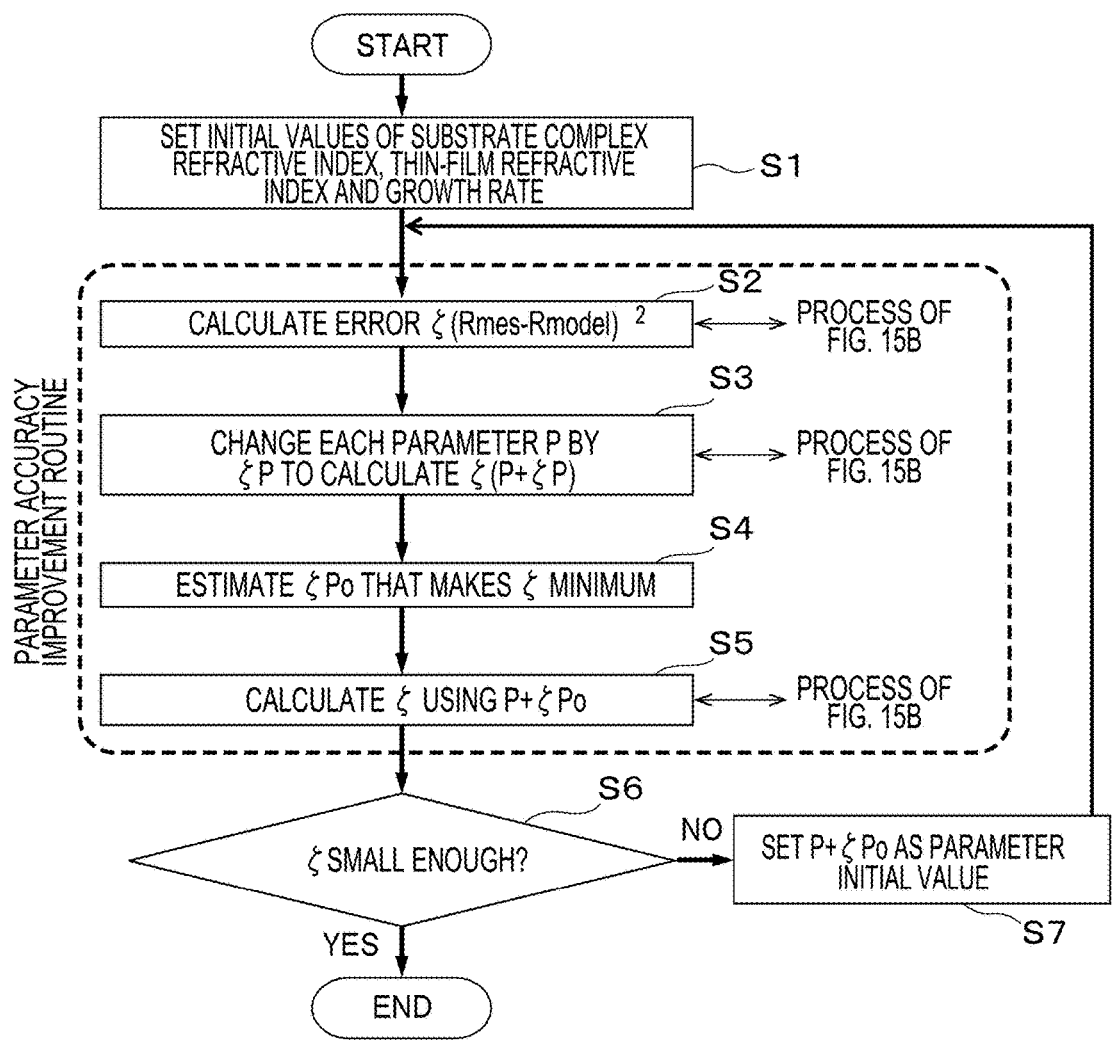
FIG. 15A is a flowchart showing an operation of a fitter.
Figure 15B:
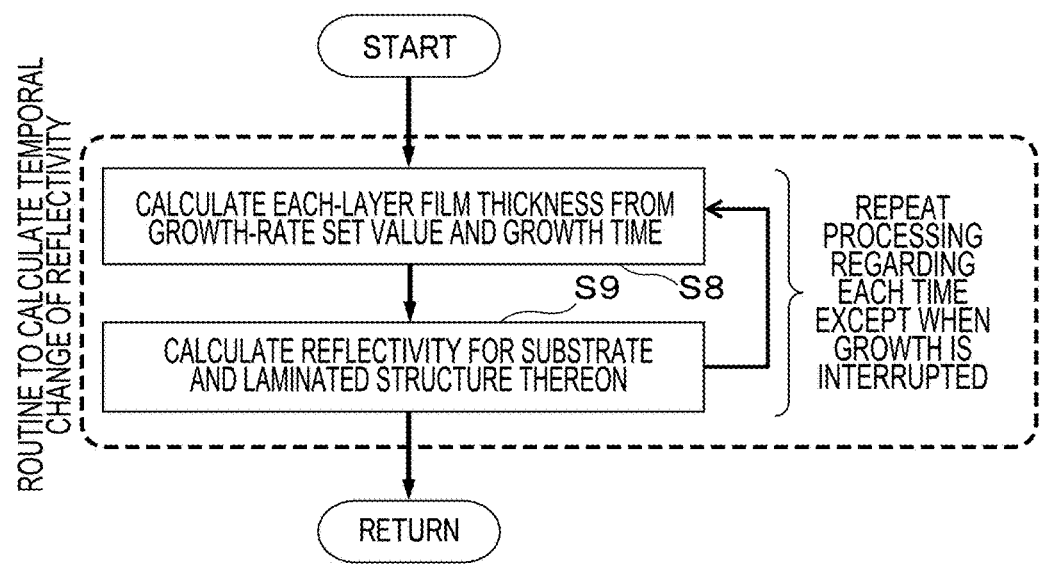
FIG. 15B is a flowchart showing a subroutine process called out of the flowchart of FIG. 15A.

FIG. 15A and FIG. 15B are flowcharts showing an example of the operation of the fitter 22. Firstly, initial values of several types of parameters (for example, a complex refractive index of a substrate, a refractive index of each thin film on the substrate, a growth rate, etc.) to be used for reflectivity model calculation are set (step S1).

Subsequently, an error between a reflectivity measured by the reflectometer and a reflectivity obtained by model calculation is calculated (step S4). The error is calculated as a total sum ($\zeta$) of differences at all reflectivity observation times, each difference being obtained by squaring a difference between a measured reflectivity (Rmes) and a reflectivity obtained by model calculation (Rmodel), at each reflectivity observation time. The total sum $\zeta$ is a function of each parameter (P) to be used in calculation and hence denoted as $\zeta(P)$.

When the process of the step S2 is executed, a subroutine process shown in FIG. 15B is called out. In the subroutine process, a film thickness of each thin film that is laminated and to be used for calculation is obtained by multiplying a growth-rate set value by a growth time (step S8). Here, the growth rate of each thin film is a fitting parameter, which is optimized with the refractive index of each thin film in accordance with an optimization process which will be described later.

Subsequently, using the complex refractive index of the substrate, and the film thickness and refractive index of each thin film, reflectivity model calculation is performed for the substrate and a laminated structure thereon (step S8). Steps S8 and S9 are repeated for every observation time except for growth suspension. In this way, model calculation is performed for reflectivity change with time from growth start to the current time (growth completion time if growth is completed). However, in the case where there are many observation times and hence it takes time more than necessary for reflectivity model function calculation, the observation times may be decimated to the extent that calculation accuracy is not lowered.

For calculation of error of reflectivity obtained by model calculation with respect to a measured value, other than the above, the method of calculating the error at each time and the method of obtaining the total sum may be changed as required. For example, for the error at each time, weighting the difference between a measured value and a calculated value in accordance with a measured reflectivity, not squaring but taking an absolute value of the difference between the measured value and the calculated value, simply taking a square root of the total sum, etc. are listed up. In the case where a difference in reflectivity between a measured value and a calculated value is equal to or larger than a prescribed value, the difference may not be included in the total sum of errors.

Subsequently, among the parameters, for a part of or all of the parameters, a small change (δP) is made from the current value (P) (step S3). For example, when the initial value of a refractive index ns is 2, the refractive index ns is changed to 2.01. This change amount is denoted as δns or the like. Here, the parameter is, for example, a refractive index ns, a growth rate ks, etc. of each thin film, which is referred to as a fitting parameter. Then, the subroutine of FIG. 15B is also called out, and Steps S8 and S9 are repeated, and an error $\zeta(P+\delta P)$ is calculated in step S3.

Several different change amounts δPq may be used to calculate $\zeta(P+\delta Pq)$ as required. In step S3, the dependency of $\zeta$ on δP is obtained approximately. Here, different refractive indexes are set for layers of different growth rates. This is because the refractive index may be different among thin films formed under the same film forming conditions except for the growth rate. However, when it is known in advance for layers that the refractive index is the same even if the growth rate is different, the same refractive index may be used for these layers. Although, the refractive index of a substrate and a thin film is a complex number in general, in the case of a transparent material, the refractive index is a real number.

Subsequently, from the dependency of $\zeta$ on δP obtained in step S3, δP (δPo) that makes $\zeta$ minimum is estimated (step S4), Subsequently, using P+δPo obtained in step S4, the subroutine of FIG. 15B is also called out to repeat Steps S8 and S9, and ζ(P+δPo) is calculated (step S5).

Subsequently, it is examined whether ζ(P+δPo) is small enough (step S6). If this value is small compared to a predetermined value, it is considered that enough fitting has been performed. On the contrary, if the value is not small compared to the predetermined value, it is considered that a parameter used in calculation has a large error. In this case, returning to step S2, the calculation is repeated with P+δPo as a new initial value (step S7). In general, the error ζ gradually becomes smaller by repeating the above-described steps S1 to S7.

The operation of the fitter 22 shown in FIG. 15A is performed per wavelength of light irradiated onto each thin film while being formed on the substrate or simultaneously performed for a plurality of wavelengths. It is a precondition in the present embodiment that reflectivity fitting is performed mainly per wavelength for reflectivity data at a plurality of wavelengths. In this case, the growth rate, the refractive index per wavelength, etc. are the fitting parameters, in which the error that has to be minimized by fitting is an error between the reflectivity data per wavelength and the reflectivity model function. On the contrary, when fitting is simultaneously performed at a plurality of wavelengths, the fitting parameters are the growth rates, refractive indexes at a plurality of wavelengths to be subjected to fitting, etc. In this case, the error that has to be minimized by fitting is an error between the reflectivity data at all wavelengths to be subjected to fitting and the reflectivity model function.

Figure 16:
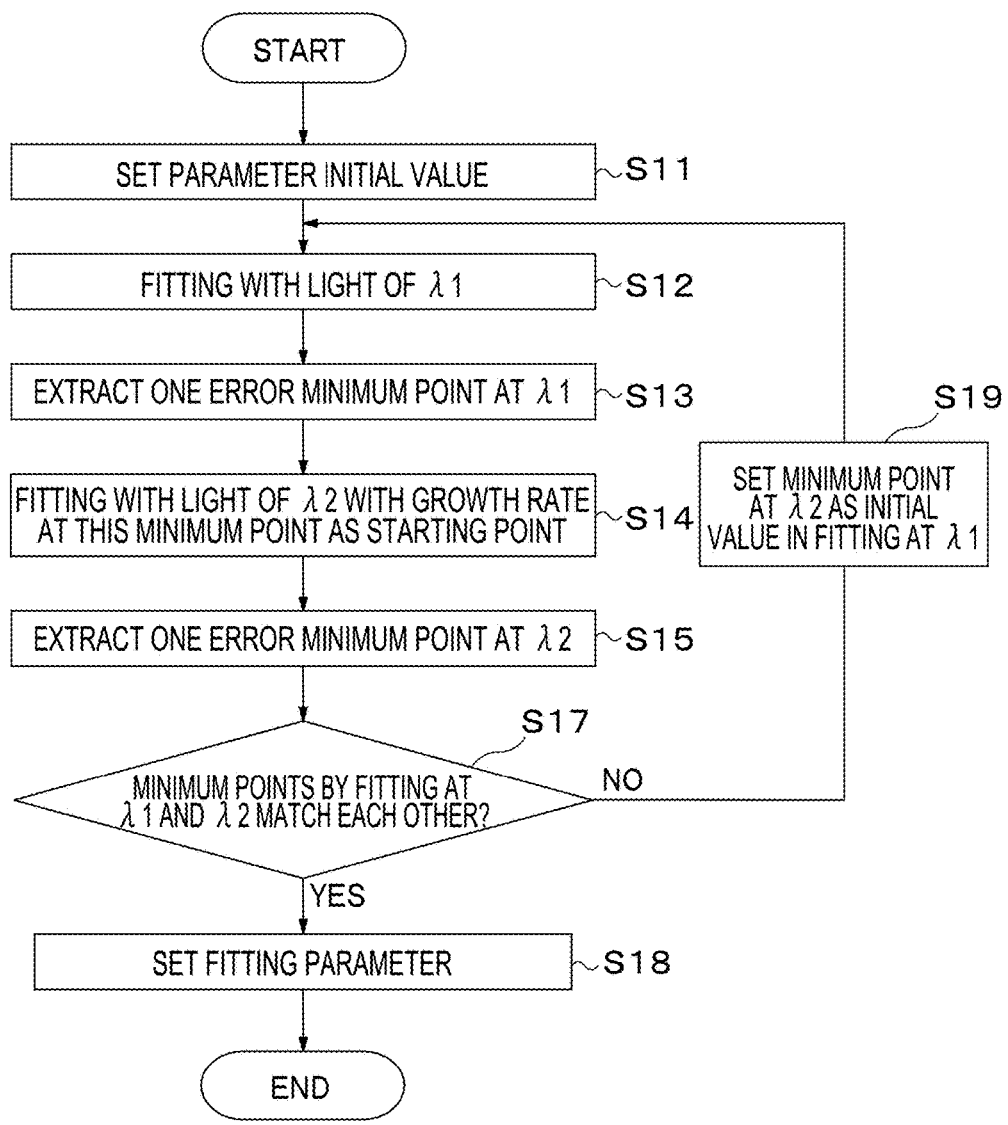
FIG. 16 is a flowchart showing an example of operations of a parameter extractor and a parameter selector, based on a process of FIG. 13.

FIG. 16 is a flowchart showing an example of the operations of the parameter extractor 23 and the parameter selector 24, based on the process of FIG. 13. The process of FIG. 16 is an example of fitting parameter selection using the two wavelengths λ1 and λ2.

First of all, light of the wavelength λ1 is irradiated onto a thin film on the substrate and a parameter initial value is set using data of reflected light from the thin film measured by the reflectometer (step S11) to make the fitter 22 perform the fitting process of FIG. 15A (step S12), in which the fitter 22 repeats the process shown in the flowchart of FIG. 15A until the error becomes small enough.

Subsequently, based on a result of step S12, the parameter extractor 23 extracts an initial error minimum point (step S13). When the initial error minimum point is extracted in step S13, using reflectivity data measured with light of the wavelength λ2, and with a parameter at the minimum point searched in step S13, as an initial value, the fitter 22 performs the fitting process of FIG. 15 (step S14).

Subsequently, the parameter extractor 23 extracts a minimum point at λ2 based on the result of a fitting process (step S14) at λ2 (step S15).

The parameter selector 24 compares the extracted minimum points for λ1 and λ2 to check whether the minimum points match each other (step S17). If the minimum points match each other, a fitting parameter is selected at the matched minimum points (step S18). If the minimum points do not match each other, a result that is extracted for λ2 is set as the initial value (step S15), and step S12 and the following steps are repeated.

When there are three wavelengths for reflectivity measurements, after extraction of a minimum point for the wavelength λ2, fitting and an error minimum-point extraction process may further be performed for a third wavelength (λ3). The same process may be performed when there are four or more wavelengths.

Figure 17:
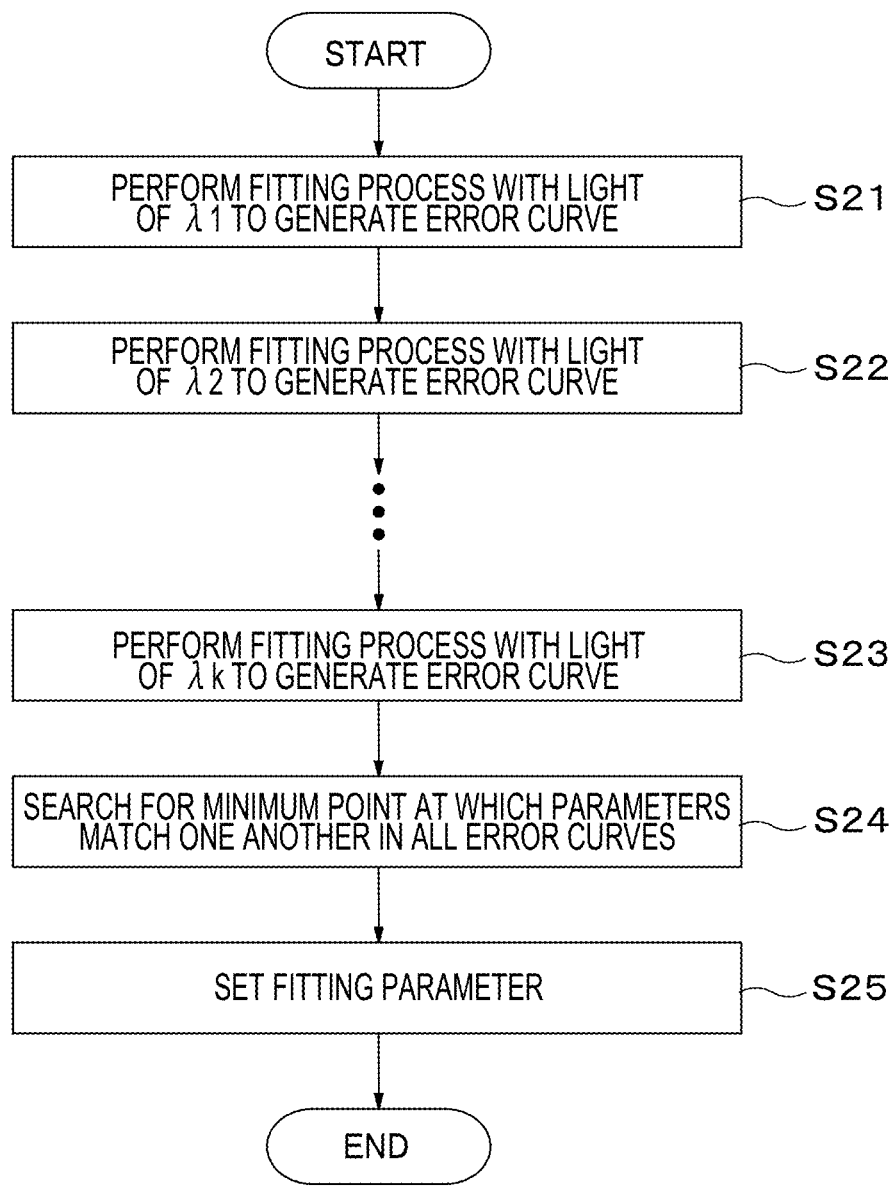
FIG. 17 is a flowchart showing an example of operations of a parameter extractor and a parameter selector, based on a process of FIG. 12.

FIG. 17 is a flowchart showing an example of the operations of the parameter extractor 23 and the parameter selector 24, based on the process of FIG. 12. The process of FIG. 17 is an example of fitting parameter selection using light of a k number of wavelengths λ1 to λk.

First of all, using light of the wavelength λ1, the fitter 22 performs the fitting process (step S21) in which the fitter 22 repeats steps S1 to S7 of FIG. 15A by a predetermined number of times until the error becomes equal to or small then a predetermined value. With this process, an error curve for the case of using light of wavelength λ1 can be obtained.

In the same manner, using light of wavelength λ2 to λk, the processes the same as step S21 are performed to obtain error curves for the case of using light of wavelength λ2 to λk (steps S22 and S23).

Subsequently, error minimum points on the error curves are compared with one another to search for the minimum points at which parameters match one another (step S24). At the searched minimum points, the parameter selector 24 selects a fitting parameter (step S25).

The example in the above is to grow a thin film of a single AlN layer on the substrate. The same method can be applied to the case where two or more layers of thin films of different materials, such as SLS of AlGaN layers and AlN layers, are formed on the substrate. However, in general, as the number of materials of thin films to be laminated increases, the parameters to be used in fitting increases. When the materials do not absorb light at a measuring wavelength, since the imaginary part of the refractive index is zero, for each of the materials, two parameters of the refractive index and growth rate are added in fitting. For the film forming temperature, two imaginary (real and imaginary parts) complex refractive indexes of the substrate are added as parameters in fitting, per film forming temperature.

In the case where a structure of a plurality of layers, such as SLS, is formed on the substrate, depending on the materials to be laminated, a film formed once may be etched away during the period from the moment at which growth is suspended once to the moment at which formation of the next layer starts (during the suspension of growth). In this case, film formation is not performed during the suspension of growth, for example, after the growth of an AlGaN thin-film layer but before the start of growth of the next AlN thin-film layer, so that the reflectivity varies a little bit even if the temperature or the like does not vary. The change in reflectivity during the suspension of growth is caused by decrease in film thickness due to the fact that the AlGaN layer is etched away during the suspension of growth. For this reason, when performing the fitting process of FIGS. 15A and 15B, it is desirable to decrease the film thickness of an AlGaN thin-film layer at the start of growth of an AlN thin-film layer, in view of the effect of etching explained above.

There is a case of varying the growth temperature depending on the layers to be laminated while continuing growth. When varying the temperature, the optical characteristics of the layers in the substrate side with respective to laminated films change, and this might cause reflectivity changes well as change in thickness of the uppermost layer does. In this case, the calculation of reflectivity based on the model function may not be performed during the temperature change, instead, comparison between a reflectivity measured value and the reflectivity model function may be performed only while the temperature is constant. However, concerning the formed film amount during the temperature change (during the suspension of calculation of the reflectivity based on the model-function), the calculation requires to be performed with properly including the formed film amount in the layers formed before or after the temperature change.

In the case of fitting process using a plurality of wavelengths such as shown in FIG. 16 or FIG. 17, it is desirable that the wavelengths are different from one another by 10% or more. When the difference in wavelength is 10% or more, it is easier to detect a correct solution because there is a remarkable difference among minimum points of incorrect solution, among minimum points on an error curve at each wavelength.

In the case where, even though the process of FIG. 16 or FIG. 17 is performed, a correct solution cannot be found out from an error curve, it is considered as its cause that each thin film formed on the substrate is not a uniform film, the value of a wavelength of light radiated onto each thin film is not accurate, or the reflectometer has a problem with accuracy, so that the reflectivity measured by the reflectometer is not accurate, and so on. Therefore, when a correct solution cannot be found out even though the process of FIG. 16 or FIG. 17 is performed, it is required to examine whether it occurs due to the above-described causes.

It is important that the substrate surface is a mirror surface when selecting the fitting parameter according to the method of the present embodiment. When a thick film is formed on the substrate surface, since interference of light is not clear, the reflectivity cannot be accurately measured and hence the accuracy is lowered. Therefore, the film thickness of a thin film, for which the fitting parameter can be selected correctly according to the present embodiment, is several ten micrometers or smaller.

The growth-rate measuring apparatus 21 according to the present embodiment is applicable to other film forming methods other than MOCVD, or to etching. The growth-rate measuring apparatus 21 according to the present embodiment is widely applicable to growth rate analysis in the case of laminating a plurality of thin films on a substrate having a mirror surface.

As described above, in the present embodiment, using a plurality of wavelengths, a reflectivity fitting process is performed for each wavelength and fitting parameters, with which a reflectivity error becomes minimum, are compared one another to select a fitting parameter. In this way, even in the case where there are a plurality of minimum points on an error curve obtained by fitting, a correct solution among the minimum points can be easily and quickly found out.

According to the present embodiment, when one minimum point is found out on an error curve at a given wavelength, by alternately performing a process of searching for minimum points on error curves at other wavelengths, a fitting parameter can be selected in a relatively short time.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

At least part of the growth-rate measuring apparatus 21 explained in the embodiment may be configured with hardware or software. When it is configured with software, a program that performs at least part of the growth-rate measuring apparatus 21 may be stored in a storage medium such as a flexible disk and CD-ROM, and then installed in a computer to run thereon. The storage medium may not be limited to a detachable one such as a magnetic disk and an optical disk but may be a standalone type such as a hard disk and a memory.

Moreover, a program that achieves the function of at least part of the growth-rate measuring apparatus 21 may be distributed via a communication network a (including wireless communication) such as the Internet. The program may also be distributed via an online network such as the Internet or a wireless network, or stored in a storage medium and distributed under the condition that the program is encrypted, modulated or compressed.

The invention claimed is:

1. A growth-rate measuring apparatus comprises:
a refractometer to irradiate light of a plurality of different wavelengths to a surface of a substrate to measure reflectivity change with time of the surface of the substrate per different wavelengths;
a fitter to fit the reflectivity calculated by a model function, the model function being obtained in advance, to a measured value of the reflectivity change with time, for at least one layer of thin films laminated one by one on the substrate, with at least one of a refractive index and a growth rate as a fitting parameter, the fitter repeatedly performing a process for fitting the reflectivity to the measured value during a growth period of the thin film;
a parameter extractor to extract sets of fitting parameters for each wavelength in the different wavelengths, respectively, for which an error between the reflectivity calculated by the model function and the measured value of the reflectivity is minimum; and
a parameter selector to select an optimum set of values of the fitting parameters, among the fitting parameters extracted for the different wavelengths.

2. The growth-rate measuring apparatus of claim 1, wherein the parameter selector sets the set of values of fitting parameters as the optimum set of values when the set of values of fitting parameters extracted for the plurality of wavelengths match one another.

3. The growth rate measuring apparatus of claim 1, wherein the parameter extractor extracts a first set of values of fitting parameters, when the error is minimum in fitting for a first wavelength among the plurality of wavelengths, and extracts a second set of values of fitting parameters for a second wavelength being different from the first wavelength based on the first set of values of fitting parameters, when the error is minimum in fitting for the second wavelength; and
the parameter selector sets the set of values of fitting parameters as the optimum set of values when the first set of values of fitting parameters and the second set of values of fitting parameters match each other.

4. The growth-rate measuring apparatus of claim 3, wherein the parameter extractor repeats fitting for the first wavelength and fitting for the second wavelength until the parameter selector selects the fitting parameter.

5. The growth-rate measuring apparatus of claim 1, wherein the fitter fits the reflectivity calculated by the model function to the measured value of the reflectivity change with time, for each light of the plurality of different wavelengths irradiated to the thin films laminated one by one, or at a same timing for the lights of the plurality of different wavelengths.

6. The growth-rate measuring apparatus of claim 5, wherein the plurality of different wavelengths have wavelength differences of 10% or more.

7. The growth-rate measuring apparatus of claim 1, wherein the parameter extractor extracts the set of values of fitting parameters in minimum points of error curves expressing a relationship between the fitting parameters and an error amount per different wavelengths.

8. The growth-rate measuring apparatus of claim 7, wherein the parameter selector selects the set of values of fitting parameters as an optimum value when the minimum points of the error curves per different wavelengths match one another.

9. A growth-rate measuring method comprises:
irradiating light of a plurality of different wavelengths to a surface of a substrate to measure a reflectivity of the surface of the substrate per different wavelengths by a refractometer;
fitting the reflectivity calculated by a model function, the model function being obtained in advance, to a measured value of the reflectivity change with time, for at least one layer of thin films laminated one by one on the substrate, with at least one of a refractive index and a growth rate as a fitting parameter, the fitting repeatedly performing a process for fitting the reflectivity to the measured value during a growth period of the thin film;
extracting sets of fitting parameters for each wavelength in the different wavelengths, respectively, for which an error between the reflectivity calculated by the model function and the measured value of the reflectivity is minimum; and
selecting an optimum set of values of the fitting parameters, among the fitting parameters extracted for the different wavelengths.

10. The growth-rate measuring method of claim 9, comprising:
fitting reflectivity calculated by the model function, the model function being obtained in advance, to a measured value of the reflectivity, for at least one layer of thin films laminated one by one on the substrate, with at least one of a refractive index and a growth rate as a fitting parameter;
extracting sets of values of fitting parameters for the different wavelengths, respectively, for which an error between the reflectivity calculated by the model function and the measured value of the reflectivity is minimum; and
selecting an optimum value of the set of values of fitting parameters, among the sets of values of fitting parameters extracted for the different wavelengths.

11. The growth-rate measuring method of claim 10, wherein the set of values of fitting parameters are set as the optimum values when the sets of values of fitting parameters extracted for the plurality of wavelengths match one another.

12. The growth-rate measuring method of claim 9, wherein a first set of values of fitting parameters are extracted when the error is minimum in fitting for a first wavelength among the plurality of wavelengths, and a second set of values of fitting parameters are extracted when the error is minimum in fitting for the first wavelength and a second wavelength based on the first set of values of fitting parameters, the second wavelength being different from the first wavelength; and
the set of values of fitting parameters are set as the optimum value when the first set of values of fitting parameters and the second set of values of fitting parameters match each other.

13. The growth-rate measuring method of claim 9, wherein fitting for the first wavelength and fitting for the second wavelength are repeated until the parameter selector selects the fitting parameter.

14. The growth-rate measuring method of claim 9, wherein the model function of the reflectivity is fitted to the measured value of the reflectivity change with time, for each light of the plurality of different wavelengths radiated to the thin films laminated one by one, or at a same timing for the lights of the plurality of different wavelengths.

15. The growth-rate measuring method of claim 14, wherein the plurality of different wavelengths have wavelength differences of 10% or more.

16. The growth-rate measuring method of claim 9, wherein the set of values of fitting parameters in minimum points of error curves expressing a relationship between the sets of values of fitting parameters and an error amount per different wavelengths is extracted.

17. The growth-rate measuring method of claim 16, wherein the sets of values of fitting parameters in a case where the minimum points of the error curves per different wavelengths match one another, as an optimum value is selected.

* * * * *